US010136827B2

(12) United States Patent
Banet et al.

(10) Patent No.: US 10,136,827 B2
(45) Date of Patent: Nov. 27, 2018

(54) HAND-HELD VITAL SIGNS MONITOR

(71) Applicant: SOTERA WIRELESS, INC., San Diego, CA (US)

(72) Inventors: Matthew J. Banet, San Diego, CA (US); Marshal Singh Dhillon, San Diego, CA (US); Andrew Stanley Terry, San Diego, CA (US); Michael James Thompson, San Diego, CA (US); Zhou Zhou, La Jolla, CA (US); Henk Visser, II, San Diego, CA (US); Adam Michael Fleming, New York, NY (US)

(73) Assignee: SOTERA WIRELESS, INC., San Diego, CA (US)

( * ) Notice: Subject to any disclaimer, the term of this patent is extended or adjusted under 35 U.S.C. 154(b) by 309 days.

(21) Appl. No.: 14/259,690

(22) Filed: Apr. 23, 2014

(65) Prior Publication Data

US 2014/0235964 A1  Aug. 21, 2014

Related U.S. Application Data

(63) Continuation of application No. 13/894,300, filed on May 14, 2013, which is a continuation of application (Continued)

(51) Int. Cl.
A61B 5/00 (2006.01)
A61B 5/0404 (2006.01)
(Continued)

(52) U.S. Cl.
CPC ............ A61B 5/0404 (2013.01); A61B 5/002 (2013.01); A61B 5/0006 (2013.01); (Continued)

(58) Field of Classification Search
CPC ......... A61B 5/02; A61B 5/0024; A61B 5/021; A61B 5/02125; A61B 5/02158;
(Continued)

(56) References Cited

U.S. PATENT DOCUMENTS 3,412,729 A   11/1968  Smith
3,868,947 A   3/1975   Holsinger
(Continued)

OTHER PUBLICATIONS

Non-Final Office Action issued by the USPTO in U.S. Appl. No. 13/894,300 dated Jul. 30, 2015.
(Continued)

Primary Examiner — Eric Winakur
Assistant Examiner — Chu Chuan (JJ) Liu
(74) Attorney, Agent, or Firm — Acuity Law Group, PC; Michael A. Whittaker

(57) ABSTRACT

The invention features a vital sign monitor that includes: 1) a hardware control component featuring a microprocessor that operates as interactive, icon-driven GUI on an LCD; and, 2) a sensor component that connects to the control component through a shielded coaxial cable. The sensor features: 1) an optical component that generates a first signal; 2) a plurality electrical components (e.g. electrodes) that generate a second signal; and, 3) an acoustic component that generates a third signal. The microprocessor runs compiled computer code that operates: 1) the touch panel LCD; 2) a graphical user interface that includes multiple icons corresponding to different software operations; 3) a file-management system for storing and retrieving vital sign information; and 4) USB and short-range wireless systems for transferring data to and from the device to a PC.

6 Claims, 7 Drawing Sheets

Related U.S. Application Data

No. 11/470,708, filed on Sep. 7, 2006, now Pat. No. 8,442,607.

(51) Int. Cl.

| | | |
|---|---|---|
| *A61B 5/0205* | (2006.01) | |
| *A61B 5/11* | (2006.01) | |
| *A61B 5/1455* | (2006.01) | |
| *A61B 5/021* | (2006.01) | |
| *A61B 5/04* | (2006.01) | |
| *A61B 5/044* | (2006.01) | |
| *A61B 7/04* | (2006.01) | |
| *A61B 5/02* | (2006.01) | |
| *A61B 5/029* | (2006.01) | |
| *A61B 5/0408* | (2006.01) | |
| *A61B 5/0402* | (2006.01) | |
| *G06F 19/00* | (2018.01) | |
| *A61B 5/08* | (2006.01) | |

(52) U.S. Cl.
CPC .......... *A61B 5/0022* (2013.01); *A61B 5/0082* (2013.01); *A61B 5/021* (2013.01); *A61B 5/0205* (2013.01); *A61B 5/02007* (2013.01); *A61B 5/029* (2013.01); *A61B 5/02055* (2013.01); *A61B 5/02125* (2013.01); *A61B 5/044* (2013.01); *A61B 5/04012* (2013.01); *A61B 5/04014* (2013.01); *A61B 5/04028* (2013.01); *A61B 5/04085* (2013.01); *A61B 5/1112* (2013.01); *A61B 5/14551* (2013.01); *A61B 5/14552* (2013.01); *A61B 5/6823* (2013.01); *A61B 5/6832* (2013.01); *A61B 5/7435* (2013.01); *A61B 5/7475* (2013.01); *A61B 7/04* (2013.01); *G06F 19/00* (2013.01); *A61B 5/04087* (2013.01); *A61B 5/08* (2013.01); *A61B 2562/063* (2013.01); *A61B 2562/166* (2013.01)

(58) Field of Classification Search
CPC ..... A61B 5/024; A61B 5/0245; A61B 5/1455; A61B 5/14552; A61B 5/00; A61B 5/0002; A61B 5/0004; A61B 5/0059; A61B 5/02416; A61B 5/0404; A61B 5/04085; A61B 5/04014; A61B 5/029; A61B 5/0006; A61B 5/044; A61B 5/7235; A61B 5/7285
USPC ....... 600/300, 301, 310, 323, 324, 437, 438, 600/473, 476, 485
See application file for complete search history.

(56) References Cited

U.S. PATENT DOCUMENTS

| | | | |
|---|---|---|---|
| 4,063,551 A | 12/1977 | Sweeny | |
| 4,080,966 A | 3/1978 | McNally et al. | |
| 4,094,308 A | 6/1978 | Cormier et al. | |
| 4,220,160 A * | 9/1980 | Kimball | A61B 7/04 600/528 |
| 4,245,648 A | 1/1981 | Trimmer et al. | |
| 4,289,141 A | 9/1981 | Cormier | |
| 4,320,767 A | 3/1982 | Villa-Real | |
| 4,367,752 A | 1/1983 | Jimenez et al. | |
| 4,380,240 A | 4/1983 | Jobsis et al. | |
| 4,424,815 A | 1/1984 | Kuntz | |
| 4,425,920 A | 1/1984 | Bourland et al. | |
| 4,653,498 A | 3/1987 | New, Jr. et al. | |
| 4,681,118 A | 7/1987 | Asia et al. | |
| 4,777,954 A | 10/1988 | Keusch et al. | |
| 4,825,879 A | 5/1989 | Tan et al. | |
| 4,846,189 A | 7/1989 | Sun | |
| 4,869,261 A | 9/1989 | Penaz | |
| 4,917,108 A | 4/1990 | Mault | |
| 4,947,859 A * | 8/1990 | Brewer | A61B 7/04 600/528 |
| 5,002,055 A | 3/1991 | Merki et al. | |
| 5,038,792 A | 8/1991 | Mault | |
| 5,054,494 A | 10/1991 | Lazzaro et al. | |
| 5,111,817 A | 5/1992 | Clark et al. | |
| 5,140,990 A | 8/1992 | Jones et al. | |
| 5,178,155 A | 1/1993 | Mault | |
| 5,179,958 A | 1/1993 | Mault | |
| 5,213,099 A | 5/1993 | Tripp, Jr. | |
| 5,237,997 A | 8/1993 | Greubel et al. | |
| 5,309,916 A | 5/1994 | Hatschek | |
| 5,316,008 A | 5/1994 | Suga et al. | |
| 5,368,039 A | 11/1994 | Moses | |
| 5,435,315 A | 7/1995 | McPhee et al. | |
| 5,485,848 A | 1/1996 | Jackson et al. | |
| 5,551,438 A | 9/1996 | Moses | |
| 5,632,272 A | 5/1997 | Diab et al. | |
| 5,649,543 A | 7/1997 | Hosaka et al. | |
| 5,687,717 A * | 11/1997 | Halpern | A61B 5/0205 600/300 |
| 5,727,558 A | 3/1998 | Hakki et al. | |
| 5,743,857 A | 4/1998 | Shinoda et al. | |
| 5,772,601 A | 6/1998 | Oka et al. | |
| 5,788,634 A | 8/1998 | Suda et al. | |
| 5,836,300 A | 11/1998 | Mault | |
| 5,857,975 A | 1/1999 | Golub | |
| 5,865,755 A | 2/1999 | Golub | |
| 5,865,758 A | 2/1999 | Louzianine | |
| 5,873,834 A * | 2/1999 | Yanagi | A61B 5/0225 600/485 |
| 5,876,348 A | 3/1999 | Sugo et al. | |
| 5,891,042 A | 4/1999 | Sham et al. | |
| 5,921,936 A | 7/1999 | Inukai et al. | |
| 6,004,274 A | 12/1999 | Nolan et al. | |
| 6,013,009 A | 1/2000 | Karkanen | |
| 6,050,940 A | 4/2000 | Braun et al. | |
| 6,176,831 B1 | 1/2001 | Voss et al. | |
| 6,224,548 B1 | 5/2001 | Gopinathan et al. | |
| 6,245,014 B1 | 6/2001 | Brainard, II | |
| 6,254,544 B1 | 7/2001 | Hayashi | |
| 6,272,936 B1 | 8/2001 | Oreper et al. | |
| 6,280,390 B1 | 8/2001 | Akselrod et al. | |
| 6,334,065 B1 | 12/2001 | Al-Ali et al. | |
| 6,336,900 B1 | 1/2002 | Alleckson et al. | |
| 6,364,842 B1 | 4/2002 | Amano et al. | |
| 6,371,921 B1 | 4/2002 | Caro et al. | |
| 6,375,614 B1 | 4/2002 | Braun et al. | |
| 6,398,727 B1 | 6/2002 | Bui et al. | |
| 6,413,223 B1 | 7/2002 | Yang et al. | |
| 6,416,471 B1 | 7/2002 | Kumar et al. | |
| 6,432,061 B1 | 8/2002 | Nissila et al. | |
| 6,443,905 B1 | 9/2002 | Nissila et al. | |
| 6,443,906 B1 | 9/2002 | Ting et al. | |
| 6,475,146 B1 | 11/2002 | Frelburger et al. | |
| 6,475,153 B1 | 11/2002 | Khair et al. | |
| 6,477,397 B1 | 11/2002 | Ronkainen et al. | |
| 6,477,405 B1 | 11/2002 | Kawaguchi | |
| 6,511,436 B1 | 1/2003 | Asmar | |
| 6,514,211 B1 | 2/2003 | Baura | |
| 6,527,711 B1 | 3/2003 | Stivoric et al. | |
| 6,533,729 B1 | 3/2003 | Khair et al. | |
| 6,546,269 B1 | 4/2003 | Kurnik | |
| 6,553,247 B1 | 4/2003 | Rytky | |
| 6,556,852 B1 | 4/2003 | Schulze et al. | |
| 6,558,321 B1 | 5/2003 | Burd et al. | |
| 6,571,200 B1 | 5/2003 | Mault | |
| 6,595,929 B2 | 7/2003 | Stivoric et al. | |
| 6,599,251 B2 | 7/2003 | Chen et al. | |
| 6,605,038 B1 | 8/2003 | Teller et al. | |
| 6,605,044 B2 | 8/2003 | Bimbaum | |
| 6,609,023 B1 | 8/2003 | Fischell et al. | |
| 6,612,984 B1 | 9/2003 | Kerr, II | |
| 6,616,613 B1 | 9/2003 | Goodman | |
| 6,645,154 B2 | 11/2003 | Oka | |
| 6,645,155 B2 | 11/2003 | Inukai et al. | |
| 6,652,466 B2 | 11/2003 | Sugo et al. | |

(56) References Cited

U.S. PATENT DOCUMENTS

| | | | |
|---|---|---|---|
| 6,678,543 B2 | 1/2004 | Diab et al. | |
| 6,681,454 B2 | 1/2004 | Modgil et al. | |
| 6,714,804 B2 | 3/2004 | Al-Ali et al. | |
| 6,723,054 B1 | 4/2004 | Baruch et al. | |
| 6,733,447 B2 | 5/2004 | Lai et al. | |
| 6,740,045 B2 | 5/2004 | Amano | |
| 6,763,256 B2 | 7/2004 | Kimball et al. | |
| 6,773,397 B2 | 8/2004 | Kelly | |
| 6,775,566 B2 | 8/2004 | Nissila | |
| 6,808,473 B2 | 10/2004 | Hisano et al. | |
| 6,813,511 B2 | 11/2004 | Diab et al. | |
| 6,814,705 B2 | 11/2004 | Kawaguchi | |
| 6,852,083 B2 | 2/2005 | Caro et al. | |
| 6,871,084 B1 | 3/2005 | Kingsley et al. | |
| 7,029,447 B2 | 4/2006 | Rantala | |
| 7,112,175 B2 | 9/2006 | Gopinathan et al. | |
| 7,128,714 B1 | 10/2006 | Antonelli et al. | |
| 8,442,607 B2 | 5/2013 | Banet et al. | |
| 8,892,196 B2 | 11/2014 | Chang | |
| 2002/0002339 A1* | 1/2002 | Sugo | A61B 5/02125 600/485 |
| 2002/0183627 A1 | 12/2002 | Nishii et al. | |
| 2003/0009108 A1* | 1/2003 | Kawaguchi | A61B 5/0285 600/528 |
| 2004/0030261 A1 | 2/2004 | Rantala et al. | |
| 2004/0199056 A1 | 10/2004 | Husemann et al. | |
| 2004/0260186 A1 | 12/2004 | Dekker | |
| 2005/0096513 A1 | 5/2005 | Ozguz et al. | |
| 2005/0192488 A1 | 9/2005 | Bryenton et al. | |
| 2006/0009691 A1 | 1/2006 | Yeo et al. | |
| 2006/0047215 A1* | 3/2006 | Newman | A61B 5/0002 600/513 |
| 2006/0056641 A1* | 3/2006 | Nadjar | A61B 7/04 381/67 |
| 2006/0100530 A1 | 5/2006 | Kliot et al. | |
| 2006/0173708 A1 | 8/2006 | Vining et al. | |
| 2008/0045813 A1* | 2/2008 | Phuah | A61B 5/0205 600/301 |

OTHER PUBLICATIONS

Bifulco et al., "Monitoring of respiration, seismocardiogram and heart sounds by a PVDF piezo film sensor", 20th IMEKO TC4 International Symposium and 18th International Workshop on ADC Modelling and Testing, Research on Electric and Electronic Measurement for the Economic Upturn, Benevento, Italy, Sep. 15-17, 2014 (4 pages).

Graham, Brian Barkley, "Using an Accelerometer Sensor to Measure Human Hand Motion", Submitted to the Department of Electrical Engineering and Computer Science in Partial Fulfillment of the Requirements for the Degrees of Bachelor of Science in Electrical Science and Engineering and Master of Engineering in Electrical Engineering and Computer Science, Massachusetts Institute of Technology, May 11, 2000 (110 pages).

Schlangel, Mark D., "Analysis of Pulse Transit Time With the Inclusion of a Microvascular Component in Head-Up Tilt and Blood Withdrawal Induced Central Hypovolemia", A Thesis Submitted to the Yale University of Medicine in Partial Fulfillment of the Requirements for the Degree of Doctor of Medicine, Yale Medicine Thesis Digital Library, Japer 206, Sep. 24, 2010 (51 pages).

Chemla et al., Short-term Variability of Pulse Pressure and Systolic and Diastolic Time in Heart Transplant Recipients. Am J Physiol Heart Circ Physiol. Jul. 2000;279(1):H122-9.

Cui et al., In Vivo Reflectance of Blood and Tissue as a Function of Light Wavelength. IEEE Trans Biomed Eng. Jun. 1990;37(6):632-639.

De Scalzi et al., Relationship Between Systolic Time Intervals and Arterial Blood Pressure. Clin Cardiol. Nov. 1986;9 (11):545-549.

Foo et al., Evaluation of Blood Pressure Changes Using Vascular Transit Time, Physiol Meas. Aug. 2006;27 (8):685-694.

Payne et al., Pulse Transit Time Measured from the ECG: an Unreliable Marker of Beat-to-Beat Blood Pressure. J Appl Physiol. Jan. 2006;100(1):136-41.

Takazawa et al, Assessment of Vasoactive Agents and Vascular Aging by the Second Derivative of Photoplethysmogram Waveform. Hypertension. Aug. 1998;32(2):365-370.

Weissler et al., Systolic Time Intervals in Heart Failure in Man. Circulation. Feb. 1968;37(2):149-159.

Final Office Action issued by the USPTO in U.S. Appl. No. 13/894,300 dated Apr. 20, 2016.

The Non Final Office Action issued by the USPTO in U.S. Appl. No. 13/894,300 dated Mar. 21, 2018 (21 pages total).

* cited by examiner

HAND-HELD VITAL SIGNS MONITOR

CROSS REFERENCES TO RELATED APPLICATION

The present invention is a continuation of U.S. patent application Ser. No. 13/894,300, filed May 14, 2013, which is a continuation of U.S. patent application Ser. No. 11/470,708 filed Sep. 7, 2006, which issued as U.S. Pat. No. 8,442,607, on May 14, 2013, which is hereby incorporated in its entirety including all tables, figures and claims.

FIELD OF THE INVENTION

The present invention relates to medical devices for monitoring vital signs, e.g. blood pressure.

DESCRIPTION OF THE RELATED ART

Pulse transit time ('PTT'), defined as the transit time for a pressure pulse launched by a heartbeat in a patient's arterial system, has been shown in a number of studies to correlate to both systolic and diastolic blood pressure. In these studies PTT is typically measured with a conventional vital signs monitor that includes separate modules to determine both an electrocardiogram (ECG) and pulse oximetry. During a PTT measurement, multiple electrodes typically attach to a patient's chest to determine a time-dependent ECG characterized by a sharp spike called the 'QRS complex'. This feature indicates an initial depolarization of ventricles within the heart and, informally, marks the beginning of the heartbeat. Pulse oximetry is typically measured with a clothespin-shaped device that clips to the patient's index finger, and includes optical systems operating in both the red and infrared spectral regions. In addition to measuring a pulse oximetry value, this method yields a time-dependent waveform, called a plethysmograph. Time-dependent features of the plethysmograph indicate both heart rate and a volumetric change in an underlying artery (e.g. in the finger) caused by the propagating pressure pulse.

In many studies PTT is calculated from the time separating the onset of the QRS complex to the foot of the plethysmograph. Alternatively, PTT can be calculated as the time separating signals measured by two sensors (e.g. optical or pressure sensors), each sensitive to the propagating pressure pulse, placed at different locations on the patient's body. In both cases, PTT depends primarily on arterial resistance, arterial compliance, the propagation distance (closely approximated by the patient's arm length), and of course blood pressure. Typically a high blood pressure results in a shorter PTT.

A number of issued U.S. Patents describe the relationship between PTT and blood pressure. For example, among others, U.S. Pat. Nos. 5,316,008; 5,857,975; 5,865,755; and 5,649,543 each teach an apparatus that includes conventional sensors that measure an ECG and plethysmograph that are processed to measure PTT. U.S. Pat. Nos. 6,511,436; 6,599,251; and 6,723,054 each teach an apparatus that includes a pair of optical or pressure sensors, each sensitive to a propagating pressure pulse, that measure PTT. As described in these patents, a microprocessor associated with the apparatus processes the PTT value to estimate blood pressure.

PTT-based measurements of blood pressure are complicated by a number of factors, one of which is the many time-dependent processes associated with each heartbeat that may correlate in a different way with blood pressure, or in fact may not correlate at all. For example, prior to the initial depolarization of the ventricles (marked by the QRS complex), the mitral valve opens and lets blood flow from the left atrium into the left ventricle. This causes the ventricle to fill with blood and increase in pressure. After the onset of the QRS, the mitral valve closes and the aortic valve opens. When the heart contracts, blood ejects into the aorta until the aortic valve closes. The time separating the onset of the QRS and the opening of the aortic valve is typically called the pre-injection period, or 'PEP'. The time separating opening and closing of the aortic valve is called the left ventricular ejection period, or 'LVET'. LVET and PEP, along with additional time-dependent properties associated with each heartbeat, are typically included in a grouping of properties called systolic time intervals, or 'STIs'.

PTT and LVET can be measured with a number of different techniques, such as impedance cardiography ('ICG') and by measuring a time-dependent acoustic waveform, called a phonocardiogram ('PCG'), with an acoustic sensor. The PCG, characterized by acoustic signatures indicating the closing (and not opening) of the mitral and aortic valves, is typically coupled with an ECG to estimate PEP and LVET. For example, U.S. Pat. Nos. 4,094,308 and 4,289,141 each teach an apparatus that measures a PCG and ECG, and from these waveforms estimates PEP and LVET. U.S. Pat. No. 7,029,447 teaches an apparatus using transit times calculated from an ICG measurement to determine blood pressure.

Studies have also shown that a property called vascular transit time ('VTT'), measured from features in both a PCG and plethysmograph, can correlate to blood pressure. Such a study, for example, is described in an article entitled 'Evaluation of blood pressure changes using vascular transit time', *Physiol. Meas.* 27, 685-694 (2006). In addition, studies have shown that PEP and LVET, taken alone, can correlate to blood pressure. These studies typically require multiple sensors placed on the patient's body to measure time-dependent waveforms that are processed to determine PEP and LVET. Studies that relate these properties to blood pressure, for example, are described in 'Systolic Time Intervals in Man', *Circulation* 37, 149-159 (1968); 'Relationship Between Systolic Time Intervals and Arterial Blood Pressure', *Clin. Cardiol.* 9, 545-549 (1986); 'Short-term variability of pulse pressure and systolic and diastolic time in heart transplant recipients', *Am. J. Physiol. Heart Circ. Physiol.* 279, H122-H129 (2000); and 'Pulse transit time measured from the ECG: an unreliable marker of beat-to-beat blood pressure', *J. Appl. Physiol.* 100, 136-141 (2006).

SUMMARY OF THE INVENTION

To address any deficiencies in the prior art, the present invention provides a hand-held vital signs monitor that combines a cuffless, PTT-based measurement of blood pressure in a device that has many of the features of a conventional personal digital assistant ('PDA'). The monitor, for example, includes a microprocessor that runs an icon-driven graphical user interface ('GUI') on a color, liquid crystal display ('LCD') attached to a touch panel. A user selects different measurement modes, such as continuous, one-time, and 24-hour ambulatory modes, by tapping a stylus on an icon within the GUI. The monitor also includes several other hardware features commonly found in PDAs, such as short-range (e.g., Bluetooth® and WiFi®) and long-range (e.g., CDMA, GSM, IDEN) modems, global positioning system ('GPS'), digital camera, and barcode scanner.

The monitor makes cuffless blood pressure measurements using a sensor that includes small-scale optical, electrical, and acoustic sensors. The sensor typically attaches to a patient's chest, just below their sternal notch. A flexible foam substrate supports the optical, electrical, and acoustic sensors and has a form factor similar to a conventional bandaid. During operation, these sensors measure, respectively, time-dependent optical, electrical and acoustic waveforms that the microprocessor then analyzes as described in detail below to determine blood pressure and other vital signs. In this way, the sensor replaces a conventional cuff to make a rapid measurement of blood pressure with little or no discomfort to the patient.

Specifically, in one aspect, the invention features a vital sign monitor that includes: 1) a hardware control component featuring a microprocessor that operates an interactive, icon-driven GUI on an LCD; and, 2) a sensor component that connects to the control component through a shielded coaxial cable. The sensor features: 1) an optical component that generates a first signal; 2) a plurality electrical components (e.g. electrodes) that generate a second signal; and, 3) an acoustic component that generates a third signal. The microprocessor runs compiled computer code that operates: 1) the touch panel LCD; 2) a graphical user interface that includes multiple icons corresponding to different software operations; 3) a file-management system for storing and retrieving vital sign information; and 4) USB and short-range wireless systems for transferring data to and from the device to a PC. The monitor can include removable memory components for storing and transporting information. For example, these components can be a flash component or a synchronous dynamic random access memory (SDRAM) packaged in a removable chip.

In other embodiments, the vital signs monitor includes a barcode scanner that reads barcodes corresponding to both patients and in-hospital operators. The monitor can also include a digital camera for taking and storing photographs, and a location-determining component (e.g. a global positioning system, or GPS) for determining the patient's location. The vital signs monitor can communicate with external devices through wireless modems that operate both short-range and long-range wireless protocols. Specifically, these modems may operate on: 1) a wide-area wireless network based on protocols such as CDMA, GSM, or IDEN; and, 2) a local-area wireless network based on a protocols such as 802.11, 802.15, 802.15.4. These protocols allow the vital signs monitor to communicate with an external computer, database, or in-hospital information system.

The vital signs monitor works in concert with the sensor to measure a patient's vital signs without using a convention blood pressure cuff. The patient typically wears the sensor on or just below the 'sternal' notch of their chest, proximal to their heart. In this location the sensor simultaneously measures, optical, electrical, and acoustic signals, which are then processed with an algorithm described below to measure blood pressure and other vital signs. The measurement is possible because: 1) the proximity of this area to the heart allows the acoustic sensor to measure the acoustic waveform; 2) an abundance of capillaries in the sternal notch, meaning the optical waveform can be measured in a reflective mode; and 3) the strong electrical activity of the heart in this area, meaning the electrical waveform can be measured with a high signal-to-noise ratio even when the electrodes are relatively close together.

In embodiments, to generate the optical waveform, the optical sensor irradiates a first region with a light source (e.g. an LED), and then detects radiation reflected from this region with a photodetector. The signal from the photodetector passes to an analog-to-digital converter, where it is digitized so that it can be analyzed with the microprocessor. The analog-to-digital converter can be integrated directly into the microprocessor, or can be a stand-alone circuit component. Typically the radiation from the light source has a wavelength in a 'green' spectral region, typically between 520 and 590 nm. Alternatively, the radiation can have a wavelength in the infrared spectral region, typically between 800 and 1100 nm. To detect this radiation, the optical sensor includes a light detector, e.g. a photodiode or phototransistor. In preferred embodiments the light source and the light detector are included in the same housing or electronic package.

To generate the electrical waveform, the electrical sensor detects first and second electrical signals with, respectively, first and second electrodes. The electrical signals are then processed (e.g. with a multi-stage differential amplifier and band-pass filters) to generate a time-dependent electrical waveform similar to an ECG. The electrical sensor typically includes a third electrode, which generates a ground signal or external signal that is further processed to, e.g., reduce noise-related artifacts in the electrical waveform. In embodiments, the electrodes are disposed on opposite ends of the substrate, and are typically separated by a distance of at least 5 cm. In other embodiments, to improve the signal-to-noise ratio, the sensor includes a third electrode connected to the electrical sensor by a cable. In other embodiments, the electrodes include an Ag/AgCl material (e.g., an Ag/AgCl paste sintered to a metal contact) and a conductive gel. Typically a first surface of the conductive gel contacts the Ag/AgCl material, while a second surface is covered with a protective layer. The protective layer prevents the gel from drying out when not in use, and typically has a shelf life of about 24 months. In still other embodiments, the electrodes are made from a conductive material such as conductive rubber, conductive foam, conductive fabric, and metal.

To generate the acoustic waveform, the acoustic sensor typically includes a microphone or piezoelectric device that measures low-frequency pressure waves (e.g. sounds) from the user's heart. This results in a time-dependent acoustic waveform that typically includes two unique 'packets' comprised of frequency components typically ranging from 40-500 Hz. The packets correspond to closing of the mitral and aortic valves. The acoustic sensor can also contact a non-conductive impedance-matching gel, such as Vaseline®, to decrease acoustic reflections at the skin/sensor interface. This typically increases the magnitude of the measured acoustic waveform.

During a measurement, the processor analyzes the various waveforms to determine one or more time-dependent parameters, e.g. VTT, PTT, PEP, or LVET, which are then further processed to determine blood pressure. The processor can further process a waveform, e.g. take a second derivative or 'fit' the rise or fall times of the optical waveform with a mathematical function, to determine additional properties relating to blood pressure. For example, in one embodiment, the microprocessor determines at least one parameter by analyzing a first point from a pulse within the optical waveform and a second point from a feature representing a heart sound within the acoustic waveform (to estimate VTT). In another embodiment, the processor determines a second parameter by analyzing a point from a QRS complex within the electrical waveform and a point from either a pulse within the optical waveform (to estimate PTT) or a point within the acoustic waveform (to estimate PEP). In yet another embodiment, the processor analyzes points representing two heart sounds from the acoustic waveform to estimate LVET.

Once these parameters are determined, the processor analyzes them with a mathematical model to determine the user's blood pressure. For example, the processor can process one or more parameters with a linear model, characterized by a slope and a y-intercept, to relate it (or them) to a blood pressure value. Alternatively, the processor can relate one or more parameters to blood pressure using a relatively complex model, such as one that includes a polynomial, exponential, or a non-linear set of equations. Once the various parameters are related to blood pressure, several 'sub-values' can be determined and concatenated into a single blood pressure value using, e.g., a pre-determined weighted average. The above-mentioned models can also use calibration values, e.g. calibration values from a cuff-based system or arterial line, to increase the accuracy of the blood pressure calculation.

The invention has a number of advantages. In general, the monitor combines all the data-analysis features and form factor of a conventional PDA with the monitoring capabilities of a conventional vital sign monitor. This results in an easy-to-use, flexible monitor that performs one-time, continuous, and ambulatory measurements both in and outside of a hospital. And because it lacks a cuff, the monitor measures blood pressure in a simple, rapid, pain-free manner. Measurements can be made throughout the day with little or no inconvenience to the user. Moreover, the optical, electrical, and acoustic sensors are integrated on a single substrate connected to the control module with a single wire. This means vital signs and related waveforms, such as blood pressure, heart rate, ECG, optical plethysmograph, and respiration rate, can be measured with a minimal amount of wires and patches connected to the patient. This can make the patient more comfortable, particularly in a hospital setting.

These and other advantages are described in detail in the following description, and in the claims.

DETAILED DESCRIPTION OF THE INVENTION

Figure 1A:
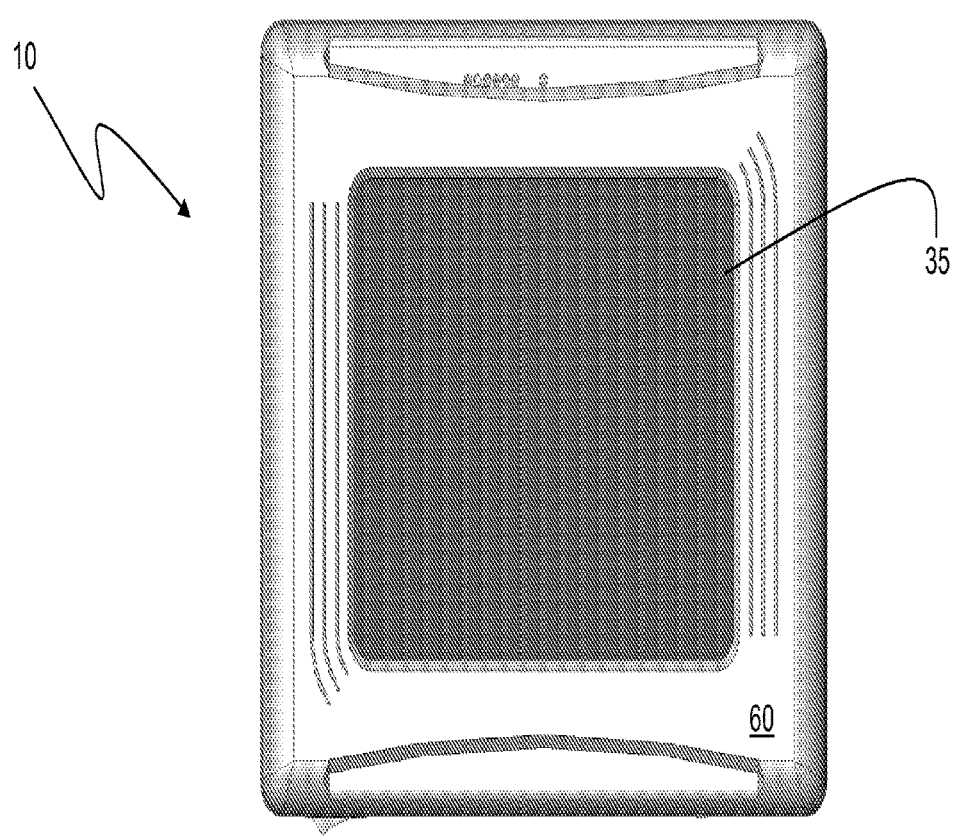
FIGS. 1A and 1B show front and top views of a vital signs monitor according to the invention.
Figure 1B:
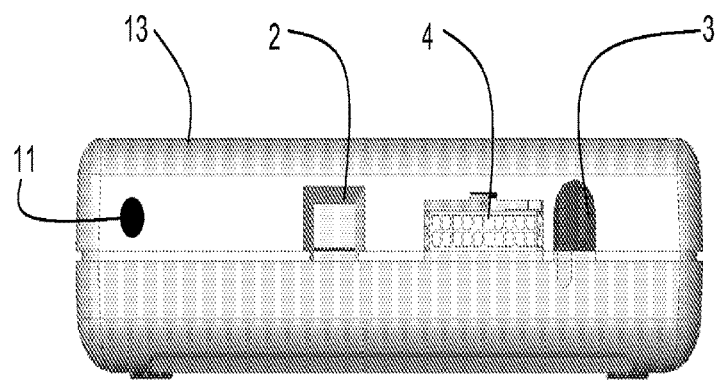
Figure 2:
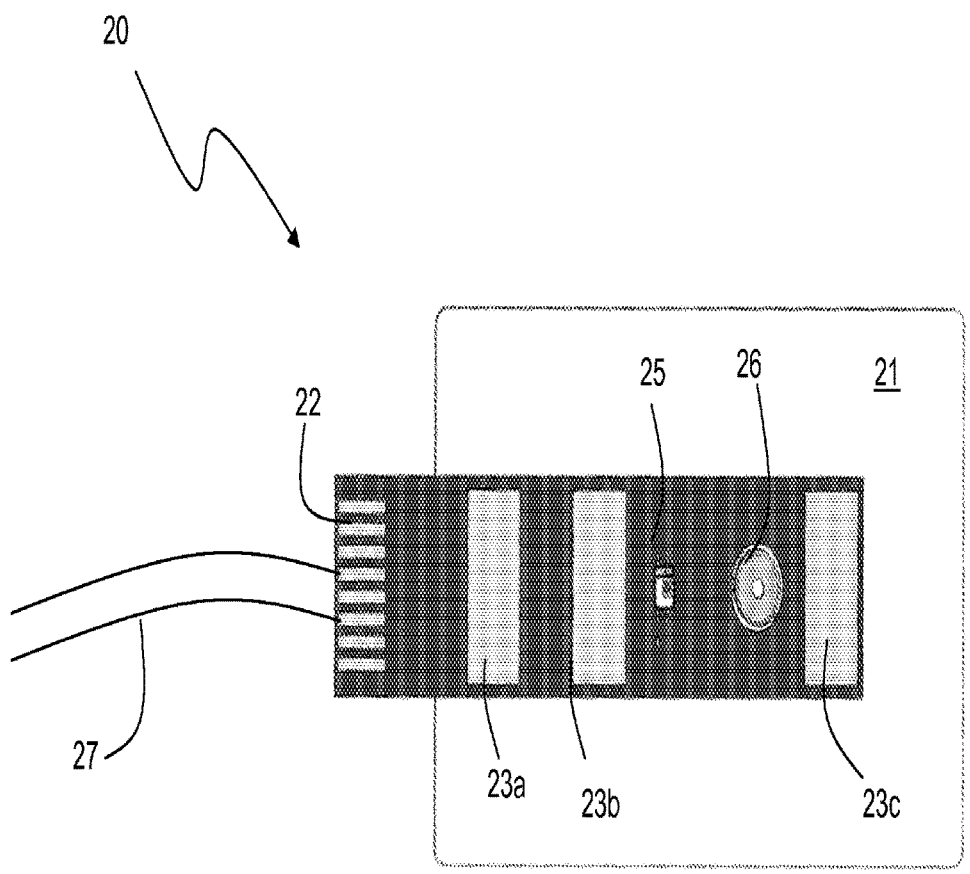
FIG. 2 shows a top view of a sensor that measures vital signs with the monitor of FIGS. 1A and 1B and includes optical electrical and acoustic sensors supported by a flexible substrate.

FIGS. 1A, 1B, and 2 show a vital signs monitor 10 according to the invention that attaches through a connector 4 and coaxial cable 27 to a sensor 20 that measures systolic and diastolic blood pressure, heart rate, respiratory rate, and ECG. Using a plastic stylus 11, an operator controls the vital signs monitor 10 through a GUI (shown in FIGS. 4A and 4B) that runs on a LCD/touch panel assembly 35. In this way, the operator can easily select a variety of different measurement modes to characterize a patient. For example, using the GUI and LCD/touch panel assembly 35, the user can select modes for one-time and continuous measurements in the hospital, as well as 24-hour ambulatory measurements and measurements made during patient transport outside of the hospital.

A plastic housing 60 surrounds the monitor 10 to protect its internal components. The monitor 10 additionally includes a barcode reader 2 to optically scan patient information encoded, e.g., on a wrist-worn barcode. A port 3 receives an external thermometer that measures a patient's esophageal temperature. The monitor 10 is lightweight, hand-held, and additionally mounts to stationary objects within the hospital, such as beds and wall-mounted brackets, through mounting holes on its back panel 13.

Referring to FIG. 2, the sensor 20 includes an adhesive foam substrate 21 that mounts a reflective optical sensor 25, piezoelectric acoustic sensor 26, and an electrical sensor featuring a primary electrode 23a, reference electrode 23b, and ground electrode 23c. These sensors measure, respectively, optical, acoustic, and electrical waveforms. During operation, analog electrical signals from each sensor 23a-c, 25, and 26 pass through a tab connector 22 that connects to the coaxial cable 27, and then through the cable 27 to an analog-to-digital converter mounted on a circuit board (shown in FIG. 3A) within the housing 60. The analog-to-digital converter digitizes these signals to generate digital waveforms, which the microprocessor then processes with an algorithm to measure blood pressure.

To reduce the effects of ambient light, the optical sensor 25 is mounted towards the middle of the foam substrate 21 and includes a light-emitting diode (LED) that typically emits green radiation ($\lambda$=520-570 nm) and a photodetector that measures reflected optical radiation which varies in intensity according to blood flow in underlying capillaries. The optical sensor 25 typically includes the LED, photodetector, and a small-scale amplifier in the same package; a preferred sensor is model TRS1755 manufactured by TAOS, Inc. of Plano, Tex. During operation, the photodetector generates a photocurrent in response to the reflected radiation, which the amplifier further amplifies before the signal passes through the tab connector 22 and coaxial cable 27. The resultant signal is similar to a conventional plethysmograph measured from a finger using a pulse oximeter.

The piezoelectric acoustic sensor 16 detects sounds waves following each of the patient's heartbeats to generate an acoustic waveform, also called a phonocardiogram. The acoustic waveform features two 'beats' that each includes a collection of acoustic frequencies. The first and second beats represent sounds made following closure of, respectively, the heart's mitral and aortic valves; these are the conventional 'lub' and 'dub' heard through a stethoscope. The preferred piezoelectric acoustic sensor is a Condenser Microphone Cartridge (manufacturer: Panasonic; part number: WM-55D103).

Concurrent with measurement of the optical and acoustic waveforms, the primary 23a, reference 23b, and ground 23c electrodes in the sensor 20 detect an electrical impulse generated in the patient following a heartbeat. This signal, which is similar to that collected with a conventional 2-lead ECG system, is registered as an analog voltage which is then digitized by the analog-to-digital converter to form the electrical waveform. The primary 23a and reference 23b electrodes are typically spaced by at least 2.5 cm to generate an electrical signal with an acceptable signal-to-noise ratio; the ground electrode 23c should be disposed at least 1 cm away from either the primary 23a or reference 23b electrode. Typically each of the electrodes includes a metal pad (e.g., a thin silver film) deposited directly on the foam substrate 21. To effectively measure electrical signals from the patient, the metal pad is typically coated with a thin layer of Ag/AgCl, which is then covered by a conductive adhesive gel.

Figure 3A:
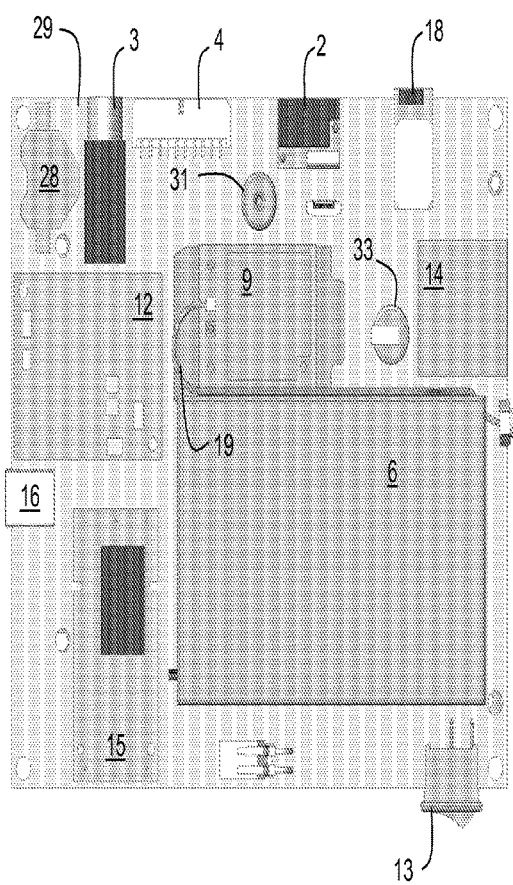
FIGS. 3A and 3B show, respectively, bottom and top views of a circuit board within the vital signs monitor of FIGS. 1A and 1B.
Figure 3B:
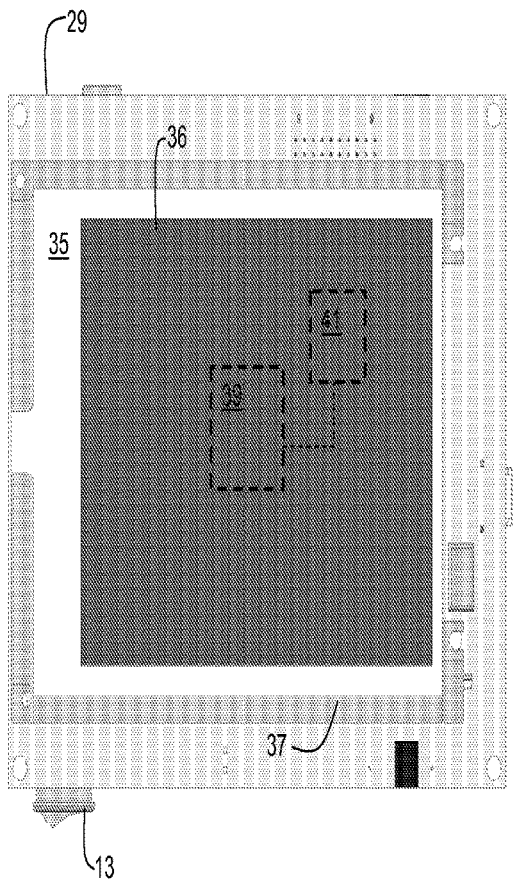

FIGS. 3A and 3B show a circuit board 29 mounted within the vital signs monitor that supports a variety of circuit elements required for the monitor to exhibit PDA-like functionality while measuring blood pressure as described above. A rechargeable lithium-ion battery 6 (manufacturer: Varta Microbattery; part number: 3P/PLF 503562 C PCM W) powers each of the circuit elements and is controlled by a conventional on/off switch 13. A smaller back-up battery 28 is used to power volatile memory components. All compiled computer code that controls the monitor's various functions runs on a high-end microprocessor 39, typically an ARM 9 (manufacturer: Atmel; part number: AT91SAM9261-CJ), that is typically a 'ball grid array' package mounted underneath an LCD display 35. Before being processed by the microprocessor 39, analog signals from the optical, acoustic, and electrical sensors pass through a connector 4 to the analog-to-digital converter 41, which is typically a separate integrated circuit (manufacturer: Texas Instruments; part number: ADS8344NB) that digitizes the waveforms with 16-bit resolution. Such high resolution is typically required to adequately process the optical, acoustic, and electrical waveforms, as described in more detail below. The microprocessor 39 also controls a pulse oximetry circuit 12 including a connector (not shown in the figure) that connects to an external pulse oximetry finger sensor. To measure temperature, a probe containing a temperature-sensitive sensor (e.g. a thermistor) connects through a stereo jack-type connector 4, which in turn connects to the analog-to-digital converter 41. During operation, the temperature-sensitive sensor generates an analog voltage that varies with the temperature sensed by the probe. The analog voltage passes to the analog-to-digital converter 41, where it is digitized and sent to the microprocessor 39 for comparison to a pre-determined look-up table stored in memory. The look-up table correlates the voltage measured by the temperature probe to an actual temperature.

After calculating vital signs, the microprocessor 39 displays them on the LCD 35 (manufacturer: EDT; part number: ER05700NJ6*B2), which additionally includes a touch panel 36 on its outer surface, and a backlight 37 underneath. An LCD control circuit 15 includes a high-voltage power supply that powers the backlight, and an LCD controller that processes signals from the touch panel 37 to determine which coordinate of the LCD was contacted with the stylus. The microprocessor 39 runs software that correlates coordinates generated by the LCD controller with a particular icon (see, e.g., FIGS. 5A and 5B), and ultimately to software functions coded into the microprocessor 39.

Information can be transferred from the monitor to an external device using both wired and wireless methods. For wired transfer of information, the circuit board 29 includes a universal serial bus (USB) connector 16 that connects directly to another device (e.g. a personal computer), and a removable SD flash memory card 14 that functions as a removable storage medium for large amounts (e.g., 1 GByte and larger) of information. For wireless transfer of information, the circuit board 29 includes both a short-range Bluetooth® transceiver 18 that sends information over a range of up to 30 meters (manufacturer: BlueRadios; part number: BR-C40A). The Bluetooth® transceiver 18 can be replaced with a transceiver that operates on a wireless local-area network, such as a WiFi® transceiver (manufacturer: DePac; part number: WLNB-AN-DP101). For long-range wireless transfer of information, the circuit board 29 includes a CDMA modem 9 (manufacturer: Wavecom; part number: Wismo Quik WAV Q2438F-XXXX) that connects through a thin, coaxial cable 19 to an external antenna 41. The CDMA modem 9 can be replaced with a comparable long-range modem, such as one that operates on a GSM or IDEN network.

The circuit board 29 includes a barcode scanner 2 (manufacturer: Symbol; part number: ED-95S-I100R) that can easily be pointed at a patient to scan their wrist-worn barcode. The barcode scanner 2 typically has a range of about 5-10 cm. Typically the barcode scanner 2 includes an internal, small-scale microprocessor that automatically decodes the barcode and sends it to the microprocessor 39 through a serial port for additional processing.

A small-scale, noise-making piezoelectric beeper 31 connects to the microprocessor 39 and sounds an alarm when a vital sign value exceeds a pre-programmed level. A small-scale backup battery 33 powers a clock (not shown in the figure) that sends a time/date stamp to the microprocessor 39, which then includes it with each stored data file.

Figure 4A:
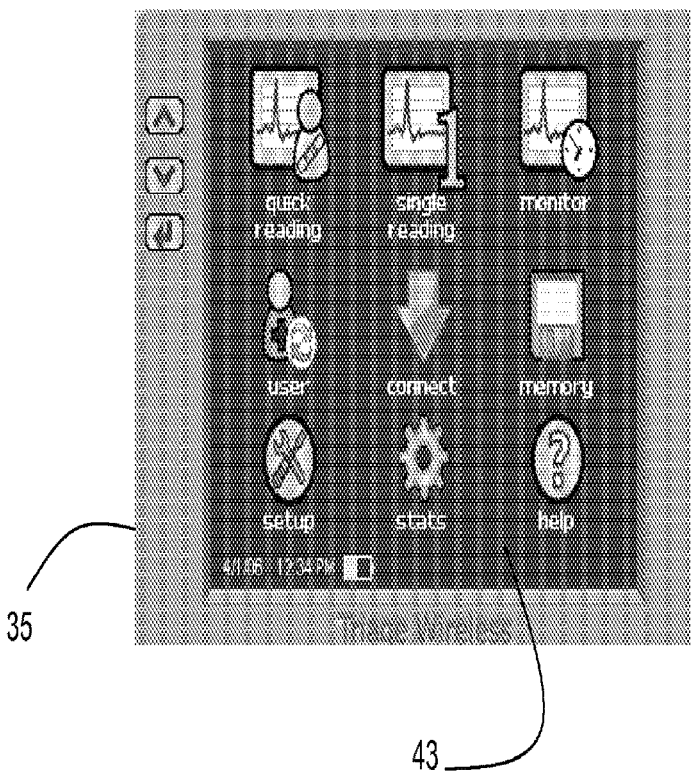
FIGS. 4A and 4B show screen captures taken from a color LCD of FIG. 3B that features an icon-driven GUI.
Figure 4B:
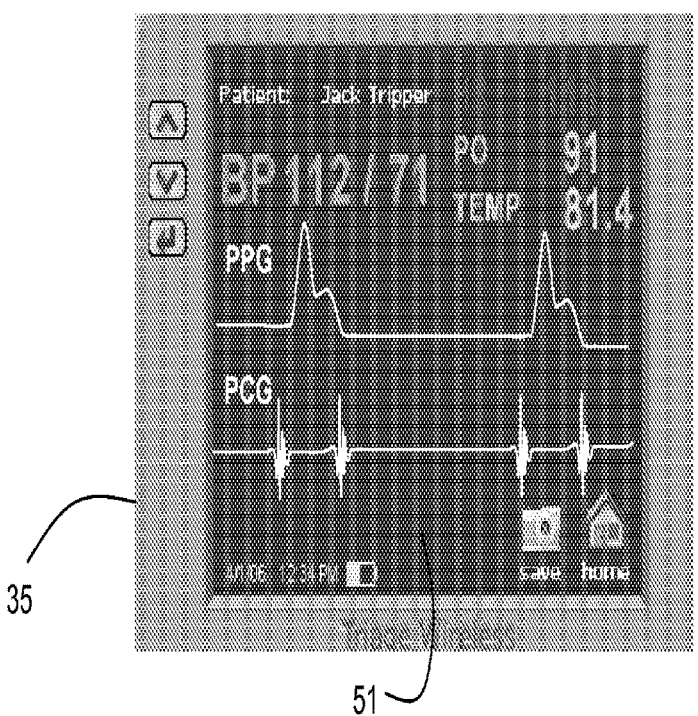

FIGS. 4A and 4B show screen captures of first and second software interfaces 43, 51 within the graphical user interface that run on the LCD 35. Referring to FIG. 4A, the first software interface 43 functions as a 'home page' and includes a series of icons that perform different functions when contacted through the touch panel with the stylus. The home page includes icons for 'quick reading', which takes the user directly to a measurement screen similar to that shown in the second software interface 51, and 'single reading', which allows the user to enter patient information (e.g. the patient's name and biometric information) before taking a measurement. Information is entered either directly using a soft, on-screen QWERTY touch-keyboard, or by using the barcode scanner. The home page also includes a 'monitor' icon which, when initiated, allows the monitor to continuously measure blood pressure and other vital signs and send them through either the short or long-range wireless transmitter to an external device (e.g., a personal computer located at a nursing station).

The home page additionally includes a 'user' icon that allows the user to enter their information through either the soft keyboard or barcode scanner. Settings on the device, e.g. alarm values for each vital sign and periodicity of measurements made during the continuous 'monitor' mode, are adjusted using the 'setup' icon. Using the 'connect' icon the user can send information from the monitor to the external device using either USB or the short-range wireless transmitter. Information can be stored and recalled from memory using the 'memory' icon, and can be analyzed with a variety of statistical algorithms using the 'stats' icon. The 'help' icon renders graphical help pages for each of the above-mentioned functions.

The second software interface 51 shown in FIG. 4B is rendered after the user initiates the 'single reading' icon in first software interface 43 of FIG. 5A. This interface shows the patient's name (entered using either the soft keyboard or barcode scanner) and values for their systolic and diastolic blood pressure, heart rate, pulse oximetry, and temperature.

The values for these vital signs are typically updated every few seconds. In this case the software interface 51 shows an optical waveform (labeled 'PPG') measured with the optical sensor, and an acoustic waveform (labeled 'PCG') measured with the acoustic sensor. These waveforms are continually updated on the LCD 35 while the sensor is attached to the patient. The second software interface 51 additionally includes smaller icons at the bottom of the LCD 35 that correspond to, respectfully, the date, time, and remaining battery life. The 'save' icon saves all the current vital sign and waveform information displayed measured by the monitor to an on-board memory, while the 'home' icon renders the first software interface 43 shown in FIG. 5A.

Figure 5:
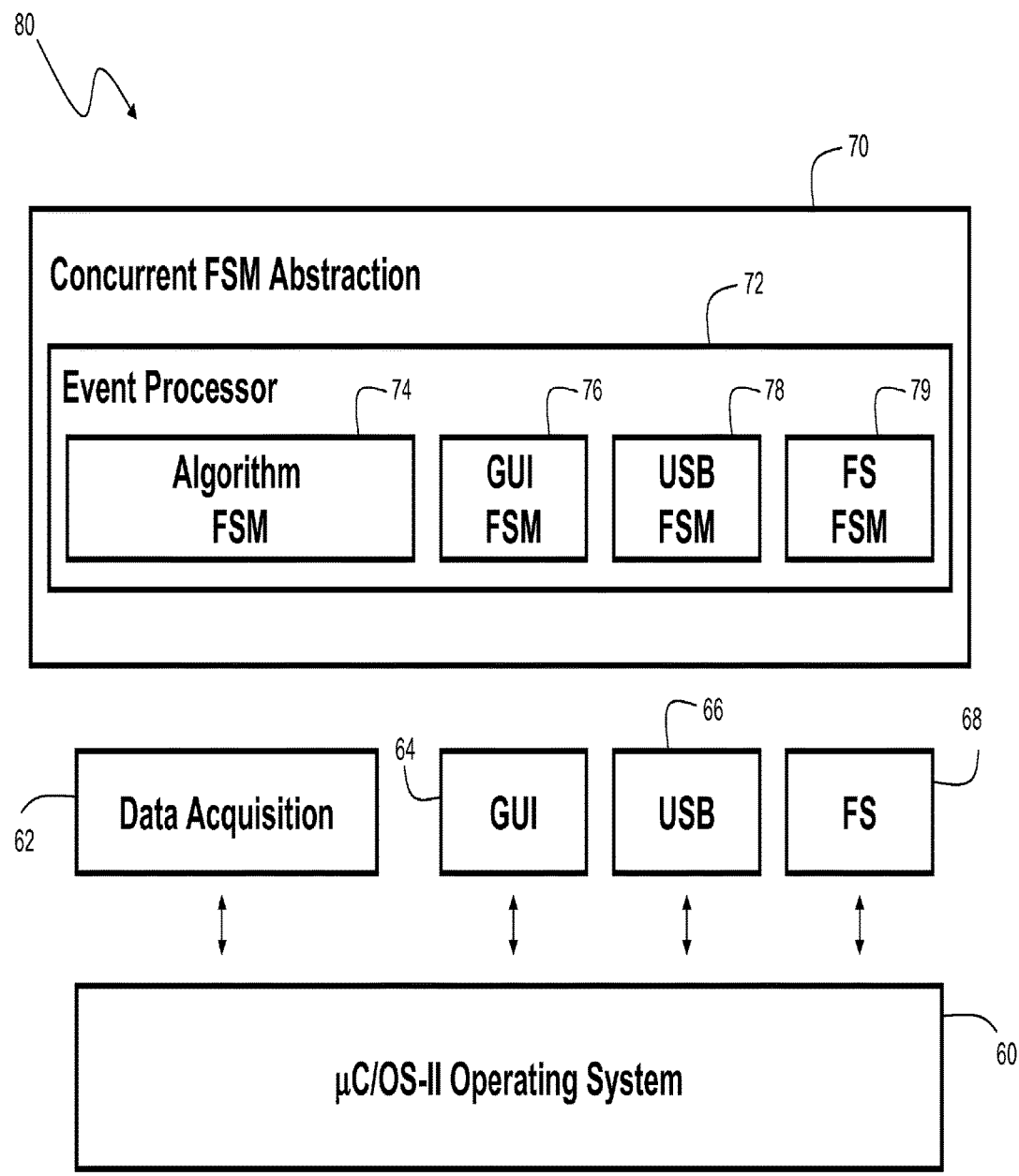
FIG. 5 shows a schematic view of an embedded software architecture used in the vital signs monitor of FIGS. 1A and 1B.

FIG. 5 shows a software architecture 80 that runs on the above-described microprocessor, allowing the monitor to measure vital signs and operate all the electrical components shown in FIGS. 3A and 3B, and run the Graphical User interface (GUI) 64 shown in FIGS. 4A and 4B. The software architecture 80 is based on an operating system 60 called the µC/OS-II (vendor: Micrium) which is loaded onto the microprocessor and operates in conjunction with software libraries (vendor: Micrium) for the GUI 64. The USB 66 library (vendor: Micrium) operates the transfer of stored patient vital signs data through a USB cable to external devices. A Microsoft Windows® compatible FAT32 embedded file management system (FS) 68 is a read-write information allocation library that stores allocated patient information and allows retrieval of information through the GUI 64. These libraries are compiled along with proprietary data acquisition code 62 library that collects of digitized waveforms and temperature readings from the analog-to-digital converter and stores them into RAM. The event processor 72 is coded using the Quantum Framework (QF) concurrent state machine framework (vendor: Quantum Leaps). This allows each of the write-to libraries for the GUI 64, USB 66, file system 68, and data acquisition 62 to be implemented as finite state machines ('FSM'), e.g. a GUI FSM 76, USB FSM 78, and file system FSM 79. Each FSM 76, 78, and 79 structure allows the user to react to an event on the GUI 64 screen during the measurement process or data retrieval. For example, the algorithm that calculates blood pressure from waveforms received through the data acquisition library 62 is implemented as an algorithm FSM 74. Each FSM 74, 76, 78, and 79 communicates with a software event processor 72 through a software protocol called 'concurrent FSM abstraction' 70. Using this architecture 80, the algorithm FSM 74, GUI FSM 76, USB FSM 78, and file system FSM 79 are implemented using low-level code included in the associated software libraries.

Figure 6:
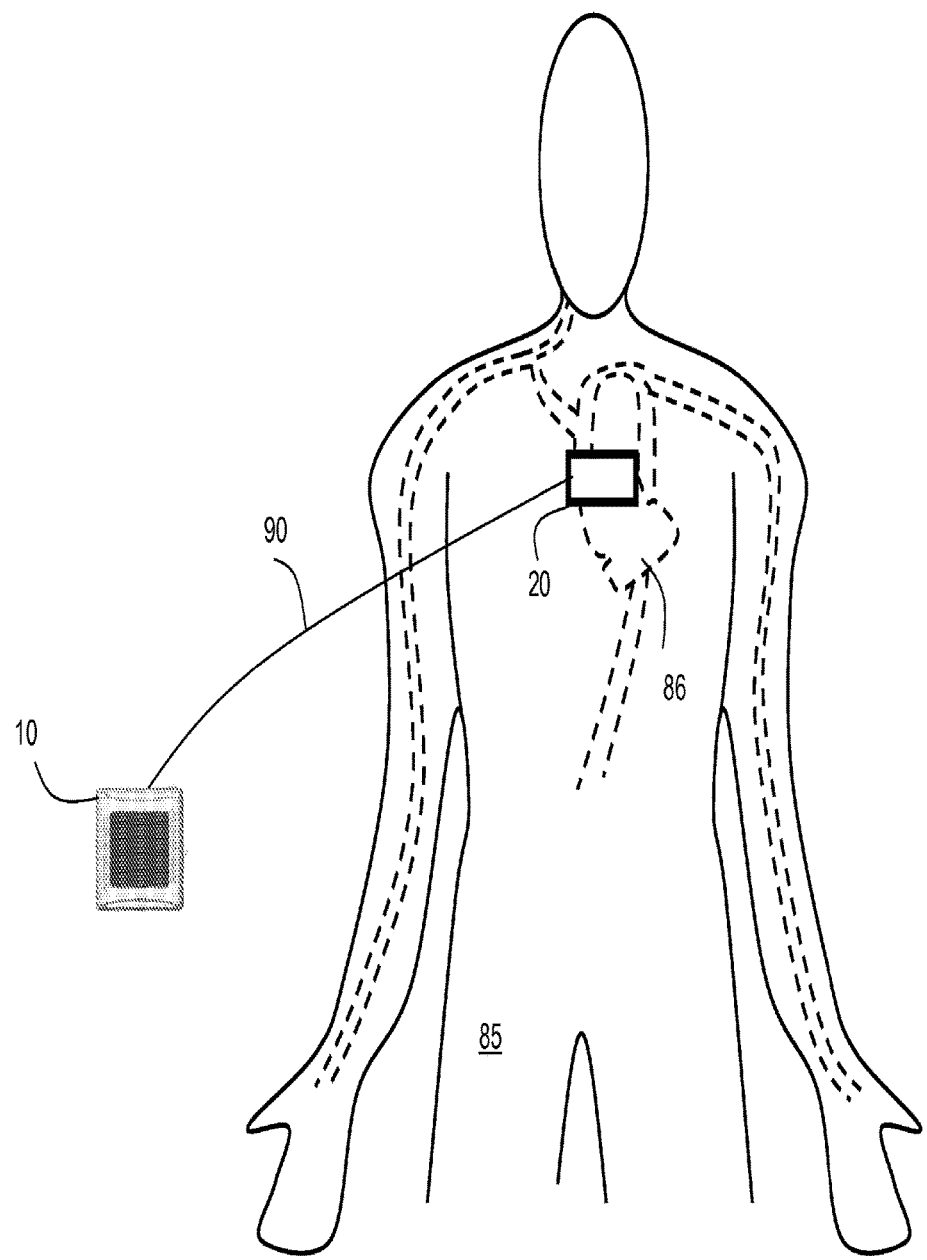
FIG. 6 shows a schematic view of the vital sign monitor of FIGS. 1A and 1B and the sensor of FIG. 2 measuring a patient near their sternal notch; and, FIG. 7 shows a schematic view of an Internet-based system used to send information from the vital signs monitor of FIGS. 1A and 1B to the Internet and an in-hospital information system.

Referring to FIG. 6, during operation, a patient's vital signs are measured while the monitor 10 is typically held by a medical professional or mounted on a bracket while the sensor 20 is adhered to the patient's chest. In this way, the sensor 20 is proximal to the patient's heart 86, a location that allows it to simultaneously measure optical, electrical, and acoustic activity that follows each heartbeat to generate the time-dependent analog waveforms described above. The waveforms propagate through shielded, co-axial wires in a cable 90 that connects the sensor 20 to the monitor 10. There, hardware and software within the monitor process the information to measure the patient's vital signs. Pulse oximetry measurements are typically made by attaching a standard pulse oximeter sensor to the patient's finger, and processing measured information the pulse oximetry circuit described with reference to FIG. 3A. Determining pulse oximetry in this way is a standard practice known in the art, and is described, for example, in U.S. Pat. No. 4,653,498 to New, Jr. et al., the contents of which are incorporated herein by reference.

In addition to those methods described above, a number of additional methods can be used to calculate blood pressure from the optical, electrical, and acoustic waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 4) VITAL SIGN MONITOR FOR ATHLETIC APPLICATIONS (U.S. Ser. No.; filed Sep. 13, 2004); 5) CUFFLESS BLOOD PRESSURE MONITOR AND ACCOMPANYING WIRELESS MOBILE DEVICE (U.S. Ser. No. 10/967,511; filed Oct. 18, 2004); and 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306,243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); and 15) SYSTEM FOR MEASURING VITAL SIGNS USING BILATERAL PULSE TRANSIT TIME (U.S. Ser. No. 11/420,652; filed May 26, 2006).

Figure 7:
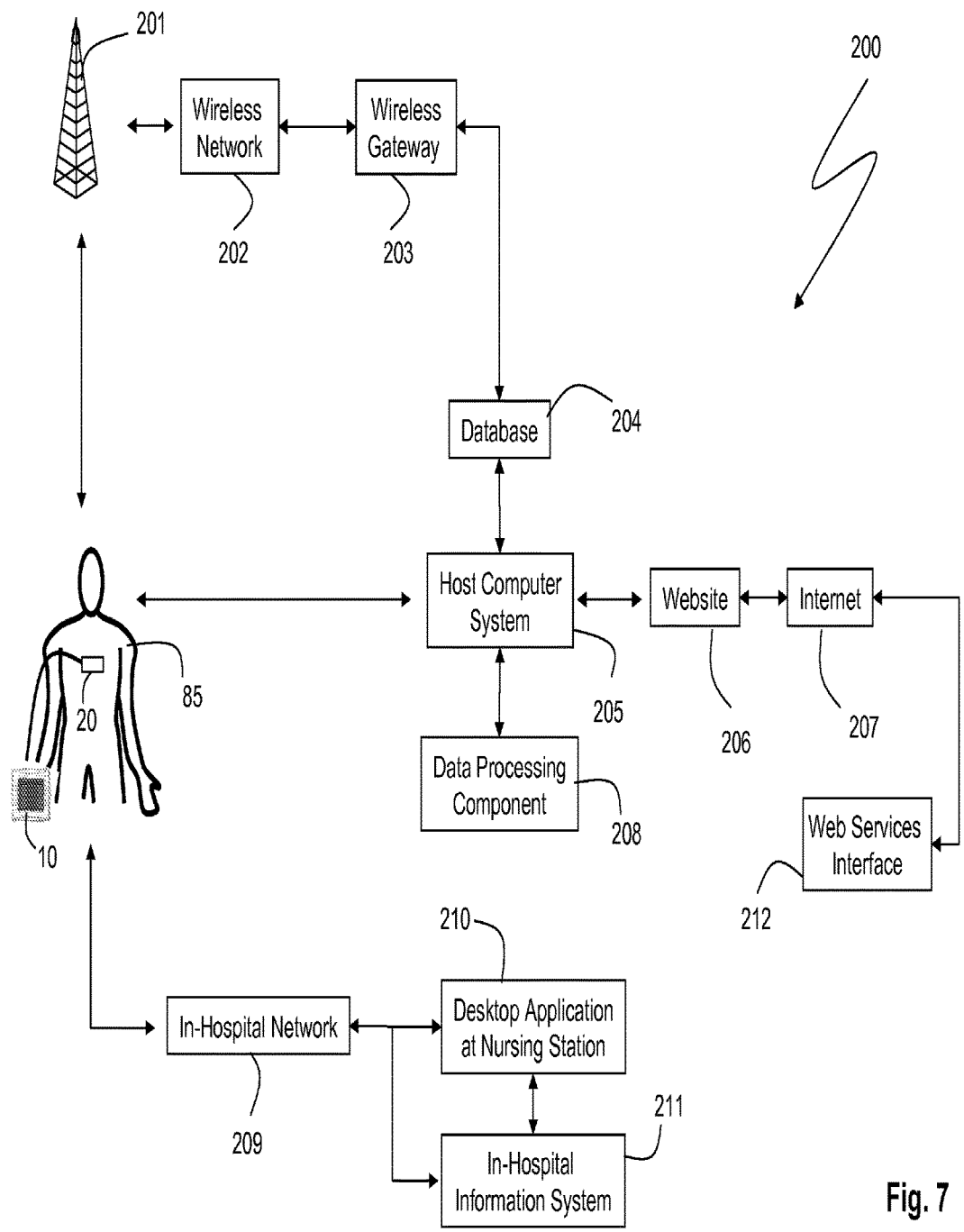

FIG. 7 shows an example of a computer system 200 that operates in concert with the monitor 10 to send information from a patient 85 to an external computer 205, 211. When the patient is ambulatory the monitor 10 can be programmed to send information to a website 206 hosted on the Internet. For example, using an internal wireless modem, the monitor 10 sends information through a series of towers 201 in a nation-wide wireless network 202 to a wireless gateway 203 that ultimately connects to a host computer system 205. The host computer system 205 includes a database 204 and a data-processing component 208 for, respectively, storing and analyzing data sent from the device. The host computer system 205, for example, may include multiple computers, software systems, and other signal-processing and switching equipment, such as routers and digital signal processors. The wireless gateway 203 preferably connects to the wireless network 202 using a TCP/IP-based connection, or with a dedicated, digital leased line (e.g., a VPN, frame-relay circuit or digital line running an X.25 or other protocols). The host computer system 205 also hosts the web site 206 using conventional computer hardware (e.g. computer servers for both a database and the web site) and software (e.g., web server, application server, and database software).

To view information remotely, the patient or medical professional can access a user interface hosted on the web site 206 through the Internet 207 from a secondary computer system such as an Internet-accessible home computer. The computer system 200 may also include a call center, typically staffed with medical professionals such as doctors, nurses, or nurse practitioners, whom access a care-provider interface hosted on the same website 206.

Alternatively, when the patient is in the hospital, the monitor can be programmed to send information to an in-hospital information system 211 (e.g., a system for electronic medical records). In this case, the monitor 10 sends information through an in-hospital wireless network 209 (e.g., an internal WiFi® network) that connects to a desktop application running on a central nursing station 210. This desktop application 210 can then connect to an in-hospital information system 211. These two applications 210, 211, in turn, can additionally connect with each other. Alternatively, the in-hospital wireless network 209 may be a network operating, e.g. a Bluetooth®, 802.11a, 802.11b, 802.1g, 802.15.4, or 'mesh network' wireless protocols that connects directly to the in-hospital information system 211. In these embodiments, a nurse or other medical professional at a central nursing station can quickly view the vital signs of the patient using a simple computer interface.

Other embodiments are also within the scope of the invention. For example, software configurations other than those described above can be run on the monitor to give it a PDA-like functionality. These include, for example, Micro C OS®, Linux®, Microsoft Windows®, embOS, VxWorks, SymbianOS, QNX, OSE, BSD and its variants, FreeDOS, FreeRTOX, LynxOS, or eCOS and other embedded operating systems. The monitor can also run a software configuration that allows it to receive and send voice calls or text messages through its embedded long-range modem. This information, for example, can be used to communicate with a patient in a hospital or at home. In other embodiments, the monitor can connect to an Internet-accessible website to download content, e.g. calibrations, text messages, and information describing medications, from an associated website. As described above, the monitor can connect to the website using both wired (e.g. USB port) or wireless (e.g. short or long-range wireless transceivers) means.

In still other embodiments, the optical, electrical, and acoustic waveforms can be processed to determine other vital signs. For example, relatively low-frequency components of an 'envelope' describing both the electrical and optical waveforms can be processed to determine respiratory rate. This can be done, for example, using an analysis technique based on Fourier Transforms. In other embodiments, the substrate can be modified to include light sources (e.g. LEDs) operating in both the red (e.g. $\lambda$=600-700 nm) and infrared ($\lambda$=800-900 nm) spectral regions. With these modifications, using techniques known in the art, that substrate can potentially measure pulse oximetry in a reflection-mode configuration. In still other embodiments, time-dependent features from the PCG can be analyzed to determine cardiac properties such as heart murmurs, lung sounds, and abnormalities in the patient's mitral and aortic valves.

Still other embodiments are within the scope of the following claims.

We claim as our invention:

1. A hand-held vital signs system, comprising:
   a housing comprising a microprocessor that is operably connected to a touch screen display on a surface of the housing to provide operation controls for the vital signs system on an icon-driven graphical user interface;
   at least two electrodes operably connected to the microprocessor configured to measure an electrical signal which is processed by the microprocessor to provide an ECG waveform; and
   a first sensor operably connected to the microprocessor configured to measure a low-frequency waveform comprising frequency components of between 40 Hz and 500 Hz indicative of heart valve operation;
   a second sensor operably connected to the microprocessor configured to measure an optical waveform,
   wherein the microprocessor is configured to collectively process the low-frequency waveform and the ECG waveform to determine a pre-ejection period, to collectively process the optical waveform, the ECG waveform and the pre-ejection period to determine a vascular transit time, and to determine a blood pressure value using the vascular transit time.

2. A hand-held vital signs system according to claim 1, wherein the system further comprises a wireless communications system configured for wireless transfer of information from the microprocessor to an external device.

3. A hand-held vital signs system according to claim 2, wherein the wireless communications system communicates with the external device by one or more of a Bluetooth protocol, a WiFi protocol, a CDMA protocol, a GSM protocol, and an IDEN protocol.

4. A hand-held vital signs system according to claim 1, wherein the at least two electrodes and the second sensor are disposed on a surface of the housing.

5. A hand-held vital signs system according to claim 1, wherein calibration information is used by the microprocessor during determination of the blood pressure value to account for arterial properties of a user of the vital signs system.

6. A hand-held vital signs system according to claim 1, wherein the first sensor is a piezoelectric sensor.

* * * * *